(12) United States Patent
Aota et al.

(10) Patent No.: US 8,889,071 B2
(45) Date of Patent: Nov. 18, 2014

(54) APPARATUS AND METHOD FOR SEPARATING PLASMA

(75) Inventors: Arata Aota, Kawasaki (JP); Takehiko Kitamori, Tokyo (JP)

(73) Assignees: Institute of Microchemical Technology Co., Ltd., Kawasaki-Shi (JP); The University of Tokyo, Tokyo (JP)

( * ) Notice: Subject to any disclaimer, the term of this patent is extended or adjusted under 35 U.S.C. 154(b) by 72 days.

(21) Appl. No.: 13/262,057

(22) PCT Filed: Dec. 7, 2009

(86) PCT No.: PCT/JP2009/070483
§ 371 (c)(1),
(2), (4) Date: Mar. 26, 2012

(87) PCT Pub. No.: WO2010/113355
PCT Pub. Date: Oct. 7, 2010

(65) Prior Publication Data
US 2012/0177537 A1    Jul. 12, 2012

(30) Foreign Application Priority Data

Mar. 31, 2009  (JP) .................................. 2009-085674

(51) Int. Cl.
*G01N 30/96*    (2006.01)
*G01N 33/00*    (2006.01)
(Continued)

(52) U.S. Cl.
CPC ............ *G01N 33/491* (2013.01); *G01N 1/4005* (2013.01)
USPC ............... 422/69; 422/73; 422/502; 422/503; 422/507; 422/527; 422/534; 422/535; 422/551; 210/645; 210/650; 210/651; 210/321.84; 210/433.1

(58) Field of Classification Search
None
See application file for complete search history.

(56) References Cited

U.S. PATENT DOCUMENTS 4,753,776 A * 6/1988 Hillman et al. ............... 422/535
5,558,834 A * 9/1996 Chu et al. ...................... 422/422
(Continued)

FOREIGN PATENT DOCUMENTS

EP          2053411 A1    4/2009
JP       2008-39615 A    2/2008
(Continued)

OTHER PUBLICATIONS

Blattert et al., "Fabrication and Testing of Novel Blood Separation Devices Based on Microchannel Bend Structures," Biomedical Applications Micro- and Nanoengineering II, Proceedings of SPIE, vol. 5651, Dec. 13-15, 2004, pp. 196-203.

(Continued)

*Primary Examiner* — Jill Warden
*Assistant Examiner* — Brittany Fisher
(74) *Attorney, Agent, or Firm* — Birch, Stewart, Kolasch & Birch, LLP

(57) ABSTRACT

An apparatus for separating plasma by which plasma can be separated from a small amount of whole blood cell sample without centrifugation is disclosed. This apparatus includes a blood channel through which blood flows; and a plasma channel through which plasma separated from said blood flows. The plasma channel is arranged at least partially in parallel with said blood channel and the blood channel and the plasma channel are at least partially in contact with each other along the longitudinal direction of the channels. Blood is made to flow at a flow rate at which blood cell components in the blood flowing through the blood channel axially accumulate and at which hemolysis does not occur. The plasma moves to the plasma channel after being separated into a blood cell layer and a plasma layer.

4 Claims, 3 Drawing Sheets

(a)

(b)

(51) Int. Cl.
*B01D 21/00* (2006.01)
*B01D 61/00* (2006.01)
*B01D 63/00* (2006.01)
*G01N 1/40* (2006.01)
*G01N 33/49* (2006.01)

(56) References Cited

U.S. PATENT DOCUMENTS

| | | | |
|---|---|---|---|
| 6,607,644 B1* | 8/2003 | Apffel, Jr. | 204/451 |
| 6,936,473 B2* | 8/2005 | Nanba et al. | 436/174 |
| 2004/0191124 A1* | 9/2004 | Noetzel et al. | 422/69 |
| 2006/0076295 A1* | 4/2006 | Leonard et al. | 210/645 |
| 2007/0082370 A1* | 4/2007 | Togawa et al. | 435/7.21 |
| 2009/0107909 A1* | 4/2009 | Kotera et al. | 210/513 |

FOREIGN PATENT DOCUMENTS

| WO | WO 2005/107939 A1 | 11/2005 |
|---|---|---|
| WO | WO 2007/136057 A1 | 11/2007 |
| WO | WO 2007/149042 A1 | 12/2007 |

OTHER PUBLICATIONS

International Search Report dated Jan. 12, 2010 for International Application No. PCT/JP2009/070483 (PCT/ISA/210).
Kobayashi et al., "Blood cells separation device using serially connected membrane filters for adapting to blood flow properties," Proceedings of the 25th Sensor Symposium, 2008 pp. 413-416.
Takahashi et al., "Micro Kessho Bunri Device no Kaihatsu," CSJ: The Chemical Society of Japan Koen Yokoshu, 1G6-49, vol. 89, No. 1, Mar. 15, 2009, p. 305.
Yang et al., "Interchannel Microstructure for separation and analyses of plasma from whole blood," 8th International Conference on Miniaturized Systems for Chemistry and Life Sciences, Malmö, Sweden, Sep. 26-30, 2004, 2 pages.
Yang, "Biological Fluid Separation in Microfluidic Channels Using Flow Rate Control," Proceedings of IMECE 2005, 2005 ASME International Mechanical Engineering Congress and Exposition, Nov. 5-11, 2005, Orlando, Florida, pp. 283-289.
Zhang et al.,"A lab-on-CD prototype for high-speed blood separation," Journal of Micromechanics and Microengineering, vol. 18, 2008, pp. 1-6.

\* cited by examiner

APPARATUS AND METHOD FOR SEPARATING PLASMA

TECHNICAL FIELD

The present invention relates to an apparatus and method for separating plasma. More particularly, the present invention relates to an apparatus and method for separating plasma which can separate plasma from a trace amount of a whole blood sample without centrifugation.

Blood analysis is an important analytical method in medical diagnosis and a variety of tests are performed using blood as a sample. Biochemical tests of blood are usually performed using plasma or serum as a sample. Plasma is prepared by collecting about 10 mL of venous blood using a syringe and centrifuging the thus collected venous blood. Since such blood collection by a syringe must be performed by a medical professional, heavy burdens are imposed upon test subjects and medical institutions, leading to an increase in the cost as well. In addition, since centrifugation is necessary, considerable labor and cost are required.

If plasma could be separated from a trace amount, for example, about several tens µL, of blood, blood collection by a syringe would not be necessary, so that test subjects themselves would be able to perform blood collection and the burdens on the test subjects and medical institutions would be reduced, and if centrifugation were not required, labor and cost would be reduced, which are desired.

There is proposed a method of separating plasma from a trace amount (about 200 µL) of blood without performing centrifugation (Non-patent Document 1). In this method, two parallel grooves having a semicircular cross-section are created on a substrate and the top portions of the two grooves are connected with each other by a channel having a depth (size) which allows plasma to pass through, but not blood cell components, and when blood is allowed to flow in one of the grooves, only plasma moves to the other groove via the channel.

However, in this method, the channel is easily clogged with blood cells and the amount of separated plasma is small. Even when diluted blood is used as a sample in order to prevent such clogging, the amount of plasma separated by this method is merely about 5% of the total plasma amount in the sample blood. In cases where a trace amount of blood is used, with an amount of plasma which can be separated being mere 5% of the total plasma amount, it is difficult to perform a variety of biochemical tests using the separated plasma as a sample because the amount of the sample is insufficient. Therefore, the above-described method is hardly practicable.

PRIOR ART DOCUMENT

Non-Patent Document

[Non-patent Document 1] X. Yang, et al., Micro TAS, 120-121, (2004)

SUMMARY OF THE INVENTION

Problems to be Solved by the Invention

An object of the present invention is to provide an apparatus and method for separating plasma which can separate plasma from a trace amount of a whole blood sample without centrifugation.

Means for Solving the Problems

The present inventors intensively studied to discover that, when blood is allowed to flow in a fine channel (hereinafter, may be referred to as "microchannel"), with appropriate settings of the dimensions of the microchannel and the blood flow rate, blood cell components flow near the center of the channel and, in the periphery of the channel, only plasma flows (axial accumulation of blood cells). Further, the present inventors discovered that, by utilizing this phenomenon, when two microchannels are arranged in contact via a filter which plasma can pass through but blood cells cannot pass through, and a whole blood is allowed to flow in one of the channels, the whole blood flows in such a manner that only the plasma component thereof is in contact with the filter, so that the plasma efficiently moves through the filter to the other microchannel without causing filter clogging; and inferred that plasma can be separated from a trace amount of a whole blood sample by utilizing this phenomenon, thereby completing the present invention.

That is, the present invention provides an apparatus for separating plasma from blood, the apparatus comprising a blood channel through which blood flows; and a plasma channel through which plasma separated from the blood flows, the plasma channel being arranged at least partially in parallel with the blood channel; wherein the blood channel and the plasma channel are at least partially in contact with each other along the longitudinal direction of the channels through the filter; blood is made to flow at a flow rate at which blood cell components in the blood flowing through the blood channel axially accumulate and at which hemolysis does not occur; and wherein plasma moves to the plasma channel after being separated into a blood cell layer and a plasma layer.

The present invention also provides a method of separating plasma from blood, the method comprising injecting blood collected from a living body via an inlet in the upstream of the blood channel of the above-described apparatus of the present invention; and recovering plasma separated from the blood via the outlet in the downstream of the plasma channel.

The present invention further provides an immunoassay apparatus for plasma as a sample, the immunoassay apparatus comprising the above-described apparatus of the present invention, in which the outlet of the plasma channel of the apparatus is connected to a sample injection port of the immunoassay apparatus.

The present invention still further provides an apparatus for separating a particle suspension into particles and liquid medium, the apparatus comprising a suspension channel through which the particle suspension is made to flow; and a medium channel through which the liquid medium separated from the particle suspension flows, the medium channel being arranged at least partially in parallel with the particle suspension channel; the suspension is made to flow at a flow rate at which particle components in the suspension flowing through the suspension channel axially accumulate; wherein the liquid medium moves to the medium channel after being separated into a particle layer and a liquid medium layer.

Effects of the Invention

By the present invention, an apparatus and method for separating plasma which can separate plasma from a trace amount of a whole blood sample without centrifugation was provided for the first time. According to the plasma separation method of the present invention, the required blood amount may be a trace amount of about 50 µL and blood collection can be performed by a test subject himself/herself, so that the burdens on the test subject and medical institution are reduced. In addition, since centrifugation is not required, labor and cost are considerably reduced. Further, the method according to the present invention has a high plasma separation efficiency and can, as specifically described in the example below, separate about 65% of the total plasma contained in a sample blood even when a whole blood is used as a sample. Therefore, even from a trace amount of sample blood, the method according to the present invention can separate plasma in an amount sufficient for performing a biochemical analysis such as immunoassay, so that the method according to the present invention can be put into practical use. Further, by the present invention, more universally without being restricted to the separation of plasma from blood, an apparatus for separating particle suspension into particles and liquid medium was provided.

DESCRIPTION OF SYMBOLS

Figure 1:
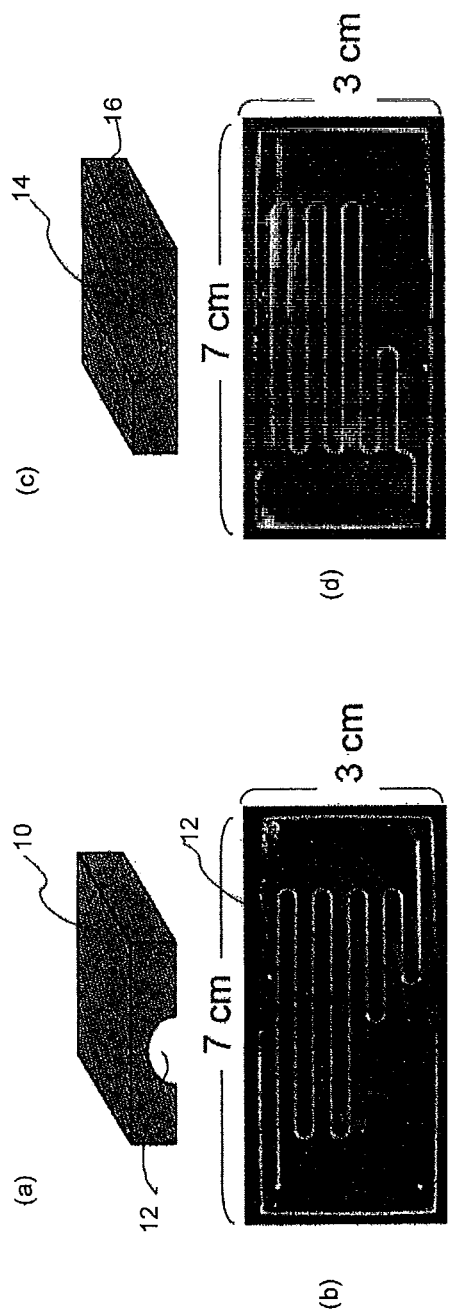
FIG. 1 is a schematic view which illustrates the above-described preferred embodiment of providing a groove-shaped blood channel and plasma channel on the respective substrates.

10: top plate (first substrate)
12: blood channel
14: plasma channel
16: bottom plate (second substrate)
18: filter
20: plasma layer

MODE FOR CARRYING OUT THE INVENTION

As described in the above, the plasma separation apparatus according to the present invention comprises a blood channel through which blood flows; and a plasma channel through which plasma separated from the blood flows, wherein the plasma channel is arranged at least partially in parallel with the blood channel. The plasma separation apparatus according to the present invention preferably further comprises a filter which isolates the blood channel and the plasma channel and has a pore size allowing plasma to pass through, but not allowing the blood cell components in the blood to pass through. In this case, the blood channel and plasma channel are at least partially in contact with each other along the longitudinal direction thereof through the filter. In a preferred mode, the blood channel and the plasma channel are microchannels each of which independently has a width of preferably 30 μm to 500 μm, more preferably 100 μm to 400 μm and a depth of preferably 10 μm to 200 μm, more preferably 50 μm to 150 μm, and the widths of the filter contacting the blood channel and plasma channel are each independently preferably 30 μm to 500 μm, more preferably 100 μm to 400 μm. Further, plasma in the blood flowing through the blood channel moves through the filter to the plasma channel.

The length of the contact between the blood channel and plasma channel through the filter is not particularly restricted; and it is preferably 1 cm to 50 cm, more preferably 10 cm to 30 cm.

The filter is not particularly restricted as long as it is one which blood cell components (erythrocyte, leukocyte and platelet) cannot pass through but plasma can pass through; and it is preferred that the filter be a hydrophilic filter having a pore size of 0.2 μm to 3 μm, more preferably 0.4 μm to 1 μm; a porosity of 5 to 20%, more preferably 7 to 18%; and a thickness of 7 μm to 22 μm, more preferably 10 μm to 15 μm. The term "hydrophilic" used herein means that water can pass through without artificial application of pressure (that is, the filter does not repel water). Examples of such hydrophilic material include resins such as polycarbonate, cellulose, alumina oxide and polyether. The preferred filter is commercially available (for example, Cyclopore (trade name) manufactured by Whatman Japan KK), and such commercially available filter can be preferably employed.

The blood channel and plasma channel are each a groove-shaped channel formed on a first and second substrate, respectively, and the first and second substrates are laminated through the filter in such a manner that the open surface of the blood channel and that of the plasma channel are at least partially in contact with each other, the filter being sandwiched between these substrates. Such a constitution is preferably adopted since the plasma separation apparatus according to the present invention can be easily and inexpensively produced. This preferred embodiment will now be described referring to the drawings.

FIG. 1 is a schematic view which illustrates the preferred embodiment of providing a groove-shaped blood channel and plasma channel on the respective substrates. FIG. 1(a) schematically shows a top plate 10, which is the first substrate on which a groove-shaped blood channel 12 having a substantially semicircular cross-section is formed. FIG. 1(b) is a bottom plan view of the top plate 10 and shows the state of the meanderingly-formed blood channel 12. In this specific embodiment, the top plate 10 is a rectangle having a size of 7 cm×3 cm; however, it is needless to say that the shape and size are not restricted thereto. The cross-sectional shape of the blood channel is not restricted to semicircle; but it is preferred that the blood channel have a semicircular or substantially semicircular cross-sectional shape (preferably, the width (diameter) is two to five times of the depth (radius)) since not only the flow becomes uniform and hemolysis is not likely to occur, but also the processing is easy. Here, the material of the top plate 10 (and the later-described bottom plate 16) is not particularly restricted as long as it does not adversely affect a test, and the material may be, for example, glass, plastic or metal. Further, in cases where the substrates are made of glass, from the standpoint of preventing leakage from the channel, it is preferred that the surfaces of the respective substrates other than those parts of the channels be modified with a water-repellent modifier such as octadecyltrichlorosilane.

FIG. 1(c) schematically shows a bottom plate 16, which is the second substrate on which a groove-shaped plasma channel 14 having a substantially semicircular cross-section is formed. FIG. 1(d) is a plan view of the bottom plate 16 and shows the state of the meanderingly-formed plasma channel 14. In this specific embodiment, the bottom plate 16 is a rectangle having a size of 7 cm×3 cm; however, it is needless to say that the shape and size are not restricted thereto. The cross-sectional shape of the plasma channel is not restricted to semicircle; but it is preferred that the plasma channel have a semicircular or substantially semicircular cross-sectional shape since the flow becomes uniform and the processing is easy.

FIG. 2(a) is an exploded perspective view which schematically shows the entirety of the preferred embodiment of providing the groove-shaped blood channel 12 and plasma channel 14 on the respective substrates, and FIG. 2(b) is a partially exploded perspective view which magnifies a part of the blood channel 12, plasma channel 14 and filter 18.

As shown in FIG. 2(a), the top plate 10 and the bottom plate 16 are laminated and the filter 18 is sandwiched therebetween. In this case, as shown in FIG. 2(b), it is preferred that the top plate 10 and the bottom plate 16 be laminated in such a manner that the open surface of the blood channel 12 and that of the plasma channel 14 are in contact with each other through the filter 18 and that the filter 18 be sandwiched between the top plate 10 and the bottom plate 16. The filter 18 may be adhered with the top plate 10 and/or the bottom plate 16 using an adhesive; however, the apparatus can be used without any problem by, for example, creating penetrating screw holes on the periphery of the top plate 10, bottom plate 16 and filter 18 and fastening bolts through the screw holes to simply sandwich the filter 18 with pressure between the top plate 10 and the bottom plate 16 without using any adhesive. As long as the blood channel 12 and the plasma channel 14 are formed on the bottom surface of the top plate 10 and the top surface of the bottom plate 16, respectively, and both of the channels have a semicircular cross-section and the same size, by positioning these channels such that they are in contact with each other and laminating the top plate 10 and the bottom plate 16, a channel having a substantially circular cross-section which is partitioned by the filter arranged in the diameter direction of the respective channels (grooves) is formed. Such an embodiment is preferred since not only the flow becomes uniform and hemolysis is not likely to occur, but also the processing is easy and the effective area of the filter 18 is large, and consequently, the plasma separation efficiency is large. Here, the widths of the blood channel 12 and the plasma channel 14 do not have to be the same; however, they are preferably the same since the effective area of the filter 18 is the largest and the highest plasma separation efficiency is attained. Accordingly, the width ratio of the blood channel 12 and the plasma channel 14 is preferably in the range of 10:8 to 8:10, most preferably 10:10.

The blood channel 12 and the plasma channel 14 may also be in contact with each other through the filter 18 in their entire lengths; however, as long as the contact has a length required for performing plasma separation, other portions do not have to be in contact. That is, the channels may be arranged at least partially in parallel with each other (in contact through the filter). As shown in FIG. 2(a), it is preferred that an outlet 12a in the downstream of the blood channel 12 and an outlet 14a in the downstream of the plasma channel 14 be arranged at least 1 cm apart from each other. By positioning the outlets of the respective channels at least 1 cm apart from each other, it is easier to arrange containers for receiving blood and plasma in separate containers. In cases where the outlets of the respective channels are arranged apart from each other in this manner, it is needless to say that the downstream portions of the respective channels are, as shown in FIG. 2(a), configured at totally different positions and are not in contact with each other through the filter 18. In addition, since a blood sample is injected only to the blood channel 12, in the vicinity of an inlet 12b in the upstream of the blood channel 12, the plasma channel 14 is not formed at the corresponding position. That is, in the uppermost stream portion of the blood channel 12 has the blood channel 12 alone.

It is noted here that, although the specific embodiment was explained using the terms "top plate" and "bottom plate" for convenience, when the apparatus is used, the "top plate" and the "bottom plate" do not have to be used on the top and bottom, respectively, and both of the substrates (the top and bottom plates) may be arranged at an arbitrary angle for use. For example, both substrates can be vertically arranged for use.

When the plasma separation apparatus according to the present invention is employed to separate plasma from blood, a sample blood is injected via the inlet 12b of the blood channel 12. The injection is preferably performed using a pump capable of easily and precisely achieving a prescribed flow rate, such as a syringe pump. When blood is allowed to flow in the blood channel 12, as indicated by the white arrows in FIG. 2(b), plasma moves from the blood channel 12 to the plasma channel 14 through the filter 18. As shown in FIG. 2(a), the plasma moved into the plasma channel 14 can be recovered from the outlet 14a of the plasma channel 14.

It is noted here that the sample blood may be diluted blood; however, as specifically described in the example below, by the method according to the present invention, even when a whole blood is used as a sample, 65% of the total plasma contained in the whole blood can be separated; therefore, the present invention is most advantageous when a whole blood is used as a sample.

Figure 3:
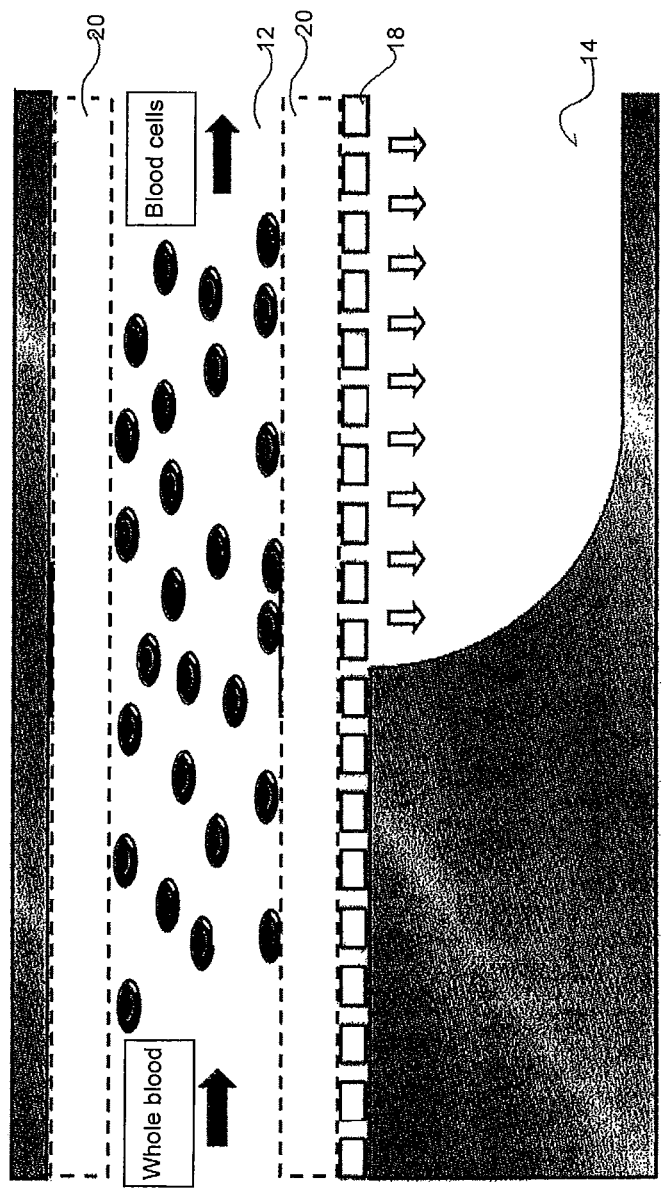
FIG. 3 is a partially enlarged schematic cross-sectional view of a preferred embodiment of the present invention which illustrates axial accumulation of blood cell components.

It is preferred that blood be allowed to flow at a flow rate at which axial accumulation of the blood cell components in the blood flowing through the blood channel 12 occurs, but at which hemolysis does not occur. Here, the axial accumulation of blood cell components is a phenomenon in which blood cell components flow near the center of a channel and, in the periphery of the channel, only plasma flows. This phenomenon is schematically shown in FIG. 3. FIG. 3 is a schematic cross-sectional view of the uppermost stream portion of the plasma channel 14. In the specific embodiment shown in the drawing, the plasma channel 14 is not arranged at the position corresponding to the uppermost stream portion of the blood channel 12, and as shown in the drawing, the plasma channel 14 starts in an intermediate portion of the blood channel 12. As schematically shown in FIG. 3, in a condition where axial accumulation of blood cell components is taking place, the blood cells flow near the center of the blood channel 12 and, in the periphery of the blood channel 12, a plasma layer in which the blood cells are substantially absent is formed. Since the filter 18 is in contact with this plasma layer 20 but not with the blood cells, clogging of the filter 18 and hemolysis caused by contact between the filter 18 and erythrocytes do not occur, so that plasma is separated at a high efficiency.

The axial accumulation can be easily attained by appropriately setting the blood flow rate once the dimensions (width, depth and length) of the blood channel 12 are decided. Needless to say, it is required that the blood flow rate be set such that hemolysis does not occur. That is, axial accumulation occurs without hemolysis at an average shear rate of 100/s to 330/s, the flow rate is set in such a manner that the average shear rate is in this range. Here, the average shear rate is represented by $4 Q/\pi/r^3$ (Q: flow rate, r: equivalent diameter). For example, in a blood channel having the dimensions adopted in the example below, that is, in a substantially semicircular channel having a width (diameter) of 300 μm and a depth (radius) of 140 μm, axial accumulation can be attained by setting the flow rate of the blood sample at 4 to 20 μL/min, preferably 5 to 12 μL/min. Whether or not axial accumulation is taking place can be examined by allowing a blood sample to flow in the blood channel 12 while observing under a microscope to determine whether or not the plasma layer in which no blood cell is seen is formed in those parts contacting the filter and the wall of the channel. Further, occurrence of hemolysis can be examined by measuring the hemoglobin concentration of the recovered plasma.

The recovered plasma can be subjected to an arbitrary biochemical test such as an immunoassay. Further, an immunoassay apparatus may also be directly connected to the outlet of the plasma channel of the apparatus according to the present invention. Immunoassay apparatus per se is well-known and a variety of automatic immunoassay apparatuses capable of performing analyses using a trace amount of plasma are commercially available and such immunoassay apparatuses may be preferably connected. In particular, there is reported an immunoassay microchip capable of performing an immunoassay on a microchannel using a trace amount of sample (Reference: T. Ohashi et al., Lab on a Chip, 9, 991-995 (2009).), and such an immunoassay microchip may also be preferably connected. Examples of subject to be examined by immunoassay include C-reactive proteins, allergies, cardiac diseases, cancers and drugs contained in blood; however, it is needless to say that the subject is not restricted thereto.

Although the apparatus described above is an apparatus for separating plasma from blood, since blood cell components in the blood are solid particles and the plasma is a liquid medium, blood is a particle suspension containing blood cell components which are particles in plasma which is a liquid medium. Accordingly, the present invention also more generally provides, without being restricted to the apparatus of separating plasma from blood, an apparatus for separating a particle suspension into particles and liquid medium, the apparatus comprising:

a suspension channel through which the particle suspension is made to flow; and a medium channel through which the liquid medium separated from the particle suspension flows, the medium channel being arranged at least partially in parallel with the particle suspension channel;

the suspension is made to flow at a flow rate at which particle components in the suspension flowing through the suspension channel axially accumulate;

wherein the liquid medium moves to the medium channel after being separated into a particle layer and a liquid medium layer. Here, the size of the particles is not restricted, and may be, for example, about 1 μm to 30 μm diameter similar to blood. The concentration of the particles in the suspension is also not restricted, and may be, for example, about 30 to 60% by weight, more particularly, 40 to 50% by weight, similar to blood. When the size and the concentration of the particles are within these ranges, the various preferred conditions and materials can also be applied here as they are.

The present invention will now be described more concretely by way of an example thereof. However, the present invention is not restricted thereto.

Preparation of Plasma Separation Apparatus

Figure 2:
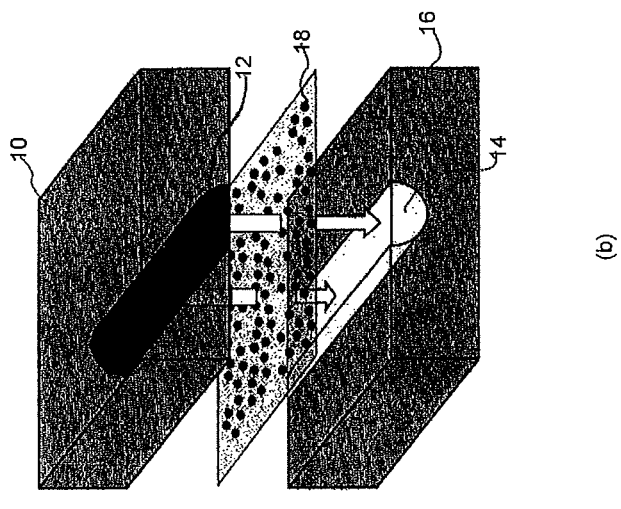
FIG. 2(a) is an exploded perspective view which schematically shows the entirety of the above-described preferred embodiment of providing a groove-shaped blood channel 12 and plasma channel 14 on the respective substrates.
FIG. 2(b) is a partially exploded perspective view which magnifies a part of the blood channel 12, plasma channel 14 and filter 18.
Figure 2:
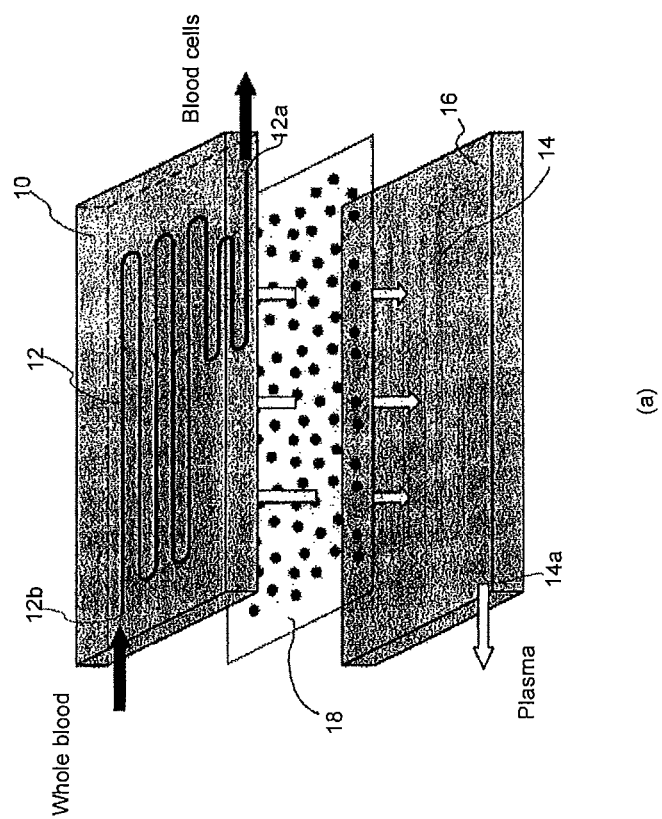

The plasma separation apparatus shown in FIGS. 1 and 2 was prepared. That is, on the bottom surface of top plate 10 made of glass, a groove (blood channel 12) having a substantially semicircular cross-section of 300 μm in width (diameter) and 140 μm in depth (radius) was formed by photolithography and wet etching. As shown in FIG. 1(b), the blood channel 12 had a meandering shape and a total length of 25 cm. On another front, on the top surface of bottom plate 16 also made of glass, a groove (plasma channel 14) having a substantially semicircular cross-section of 300 μm in width (diameter) and 140 μm in depth (radius) was formed in the same manner as in the case of the blood channel 12. As shown in FIG. 1(d), the plasma channel 14 had a meandering shape and a total length of 25 cm. The top plate 10 and the bottom plate 16 were both a rectangle having a size of 7 cm×3 cm. Further, the surfaces of the respective glass plates other than those parts of the channels were subjected to water-repellent treatment with octadecyltrichlorosilane.

A polycarbonate filter 18 (trade name: Cyclopore; manufactured by Whatman Japan KK) having a pore size of 0.4 μm, a thickness of 15 μm and a porosity of 10% was placed on the bottom plate 16 and the top plate 10 was laminated on the filter 18. In this case, as shown in FIG. 2(b), the top plate 10 and the bottom plate 16 were laminated in such a manner that the bottom surface of the blood channel 12 was in contact with the top surface of the plasma channel 14 through the filter 18 (the top plate 10 and the bottom plate 16 are both a rectangle having the same size, and the blood channel 12 and the plasma channel were formed in such a shape that the bottom surface of the blood channel 12 were in contact with the top surface of the plasma channel 14 through the filter 18 when the rectangle plates were tightly overlapped). Bolts were threaded through a plurality of penetrating screw holes (not shown) formed on the periphery of the top plate 10, filter 18 and bottom plate 16 to sandwich the filter 18 between the top plate 10 and the bottom plate 16, thereby completing the preparation of the apparatus according to the present invention.

Using a syringe pump, 100 μL of a whole blood was injected via the inlet 12b of the blood channel at a flow rate of 5 μL/min (average shear rate: 110/s) or 10 μL/min (average shear rate: 220/s), and plasma was recovered from the outlet 14a of the plasma channel. When the volume of the thus recovered plasma was measured to calculate the ratio of the amount of the recovered plasma with respect to the total plasma, the ratio was determined to be about 65% for both flow rates. Further, when the hemoglobin concentration of the recovered plasma was determined by measuring the absorbance thereof, the hemoglobin concentration was 0.0 g/dL in both cases; therefore, it was shown that hemolysis did not occur.

INDUSTRIAL APPLICABILITY

The apparatus and method for separating plasma according to the present invention can separate plasma from a trace amount of a whole blood sample without centrifugation; therefore, they can be suitably utilized in a variety of blood chemical tests using blood collected from a living body as a sample.

The invention claimed is:

1. A method of separating plasma from blood, said method comprising:

providing an apparatus for separating plasma from blood, said apparatus comprising:
a blood channel through which blood flows; and
a plasma channel through which plasma separated from said blood flows, said plasma channel being arranged at least partially in parallel with said blood channel;
wherein said blood channel and said plasma channel are at least partially in contact with each other along the longitudinal direction of said channels through a filter;
wherein said blood channel and said plasma channel are in contact with each other through said filter through which said blood cell components cannot pass but said plasma can pass; and
wherein said blood channel is a groove-shaped channel formed on a first substrate and said plasma channel is a groove-shaped channel formed on a second substrate, said first and second substrates being laminated through said filter in such a manner that an open surface of said blood channel and that of said plasma channel are at least partially in contact with each other, said filter being sandwiched between said substrates, and wherein the blood channel and the plasma channel each independently have a width of 30 μm to 500 μm and a depth of 10 μm to 200 μm, injecting blood collected from a living body via an inlet in the upstream of said blood channel of the apparatus at an average shear rate of 100/s to 330/s, so that blood cell components in said blood flowing through said blood channel axially accumulate, hemolysis does not occur, and plasma moves to said plasma channel after being separated into a blood cell layer and a plasma layer; and recovering plasma separated from said blood via said outlet in the downstream of said plasma channel.

2. The method according to claim 1, wherein said blood is whole blood.

3. The method according to claim 1, wherein said blood injected has an amount of 20 μL to 500 μL.

4. The method according to claim 1, wherein the blood is injected at a flow rate of 5 to 12 μL/min.

\* \* \* \* \*